US007825568B2

(12) United States Patent
Andle (10) Patent No.: US 7,825,568 B2
(45) Date of Patent: Nov. 2, 2010

(54) ELECTRO ACOUSTIC SENSOR FOR HIGH PRESSURE ENVIRONMENTS

(75) Inventor: Jeffrey C Andle, Falmouth, ME (US)

(73) Assignee: Vectron International, Inc., Hudson, NH (US)

(*) Notice: Subject to any disclaimer, the term of this patent is extended or adjusted under 35 U.S.C. 154(b) by 626 days.

(21) Appl. No.: 11/814,074

(22) PCT Filed: Apr. 20, 2006

(86) PCT No.: PCT/US2006/015510
§ 371 (c)(1),
(2), (4) Date: Jul. 16, 2007

(87) PCT Pub. No.: WO2007/123537
PCT Pub. Date: Nov. 1, 2007

(65) Prior Publication Data
US 2009/0309453 A1    Dec. 17, 2009

(51) Int. Cl.
H01L 41/04    (2006.01)
H01L 41/047    (2006.01)
(52) U.S. Cl. ............... 310/333; 310/313 R; 310/320; 310/366
(58) Field of Classification Search ......... 310/313 R, 310/313 A, 313 B, 313 C, 313 D, 324, 330–332, 310/338, 365, 366, 320, 333
See application file for complete search history.

(56) References Cited

U.S. PATENT DOCUMENTS

| 4,175,243 A * | 11/1979 | Corbett ............... 310/338 |
| 4,312,228 A | 1/1982 | Wohltjen |
| 4,535,631 A | 8/1985 | Shina |
| 4,769,882 A * | 9/1988 | Rosen et al. ............... 29/25.35 |
| 5,565,724 A | 10/1996 | Hachigo et al. |
| 5,633,616 A | 5/1997 | Goto |
| 5,877,581 A | 3/1999 | Inoi et al. |
| 5,880,552 A * | 3/1999 | McGill et al. ............ 310/313 R |
| 6,378,370 B1 | 4/2002 | Haskell et al. |
| 7,514,844 B2 * | 4/2009 | Unkrich ............... 310/317 |
| 7,666,152 B2 | 2/2010 | Ein-Gal |
| 2006/0244346 A1 * | 11/2006 | Iwata ............... 310/368 |

OTHER PUBLICATIONS

R.L. Baer, C.A. Flory, M. Tom-Moy and D.S. Solomon, "STW Chemical Sensors," Proc. 1992 Ultrasonics Symp., pp. 293-298 (1991).

(Continued)

*Primary Examiner*—Walter Benson
*Assistant Examiner*—Derek J Rosenau
(74) *Attorney, Agent, or Firm*—Shalom Wertsberger; Saltamar Innovations (57) ABSTRACT

A composite acoustic wave device (AWD) which is adapted for operation at high ambient pressures is provided. The AWD comprises two piezoelectric plates in back to back relationship, with electrodes disposed between the plates. The plates are bonded so as to neutralize the effects of external pressure. Further disclosed is a sensor utilizing the AWD and methods for utilizing such AWD for physical measurements in high pressure environments. An optional cavity formed between the piezoelectric plates offers the capability to measure the pressure and to further neutralize the residual effects of the pressure on measurement accuracy.

25 Claims, 6 Drawing Sheets

OTHER PUBLICATIONS

Takahiro Inoue, Masahiro Yoshimatsu, and Masanobu Okazaki, "Miniaturization of Angular Rate Sensor Element Using Bonded Quartz Tuning Fork", Proceedings of the 2003 IEEE International Frequency Control Symposium and PDA Exhibition Jointly with the 17th European Frequency and Time Forum, 2003.

Arthur Ballato, Theodore Lukaczek, "Stacked Crystal Filters", Proceedings of the IEEE, Oct. 1973, IEEE.

Arthur Ballato, "The Stacked-Crystal Filter", Proceedings, 1975 IEEE international Symposium on Circuits and Systems, Apr. 1975, IEEE.

Gandsas et al., "Advanced Therapy in Minimally Invasive Surgery", (Talmini, © 2006 BC Decker of Hamilton, ON, Canada, ISBN 1-55009-238-3).

Shri S. Shankar, "Well Logging Techniques And Formation Evaluation- An Over View", US Department of Energy report EM 1110-1-1802, "Engineering and Design—Geophysical Exploration for Engineering and Environmental Investigations".

Hata & Shimizu, "Unidirectional surface-acoustic-wave transducer with meander and interdigital electrodes", Electronics and Communications in Japan, vol. 61, Jul. 1978, p. 52-60.

* cited by examiner

ELECTRO ACOUSTIC SENSOR FOR HIGH PRESSURE ENVIRONMENTS

FIELD OF THE INVENTION

This invention relates generally to electro-acoustic sensors and more particularly to an electro-acoustic sensor capable of operating within high pressure environments.

BACKGROUND OF THE INVENTION

Piezoelectric sensors are well known. They are used for sensing material properties such as viscosity and density, for detecting the presence of certain materials in an environment, for measuring purity of fluid substance, and the like. Structures known for acoustic sensing range from the simple crystal resonator, crystal filters, acoustic plate mode devices, Lamb wave devices, and the like. Briefly, these devices comprise a substrate of piezoelectric material such as quartz, langasite or lithium niobate, or thin films of piezoelectric material, such as aluminum nitride, zinc oxide, or cadmium sulfide, on a non-piezoelectric substrate. The substrate has at least one active piezoelectric surface area, which is highly polished. Formed on the surface are input and output transducers for the purpose of converting input electrical energy to acoustic energy within the substrate and reconverting the acoustic energy to an electric output signal. These transducers may consist of parallel plate (bulk wave) or periodic interdigitated (surface-generated wave) transducers. It is noted that a single transducer may act both as the input and the output transducer.

Each of the afore-mentioned sensors can be designed to operate while being fully immersed in the fluid. However the sensitive electronics are then subjected to, in the least, noise signals and reading errors and, in the extreme, to corrosion or even explosive hazards. Passivation of the electronics surface is well known and is suitable in some limited applications, as seen for the Love Wave and surface transverse wave (STW) sensors, and such are described for example by R. L. Baer, C. A. Flory, M. Tom-Moy and D. S. Solomon, "STW Chemical Sensors," Proc. 1992 Ultrasonics Symp., pp. 293-298 (1991). However passivation is not complete and electrical components of the circuit are still exposed to capacitive loading and noise injection. Moreover, most passivation methods require the use of material having poor acoustic characteristics compared to single crystal materials. Finally, these passivated STW sensors exhibit undesirably high shear rate for many liquid phase measurements. While such sensors potentially address many sensor applications, they are not ideal, for instance, in measuring fluids in oil production, especially in down-well environments.

In most applications the surface opposite the transducers is in direct or indirect contact with the fluid being measured and interfaces acoustic energy to and from it. In addition to the interface function, the piezoelectric material forms a protective membrane between the fluid and a cavity containing electrical components of the sensor. As the volume behind the piezoelectric material is commonly not pressurized to the same level of the fluid, the piezoelectric material is exposed to the pressure difference between the fluid and the pressure within the cavity. Therefore, the finite strength of the material limits the operating pressure to which the sensor may be exposed. Even if the material is sufficiently strong to withstand the pressure, the nonlinear effect on the sensor of membrane flexure will severely affect the sensor characteristics.

On the other hand many technology areas may benefit from measuring fluid with low sensitivity to pressure variations or at high pressure levels. Examples of such technologies include by way of a non-limiting example, gas production, oil well and oil pipes, hydraulic systems, injection molding equipment, anti terror detection system for detection of biological and chemical substances, and the like. Therefore there is a long felt and heretofore unanswered need in the industry for an electro acoustic sensor capable of operating with low sensitivity to pressure variations, and/or in high ambient pressure environments. The present invention is directed to a solution to that need.

SUMMARY OF THE INVENTION

It is therefore an object of the present invention to provide a sensor where the probe may be immersed so as to experience isobaric pressure. Such a sensor would experience pressure effects at a much-reduced level due only to the nonlinear elastic constants of the piezoelectric material rather than to the more prominent flexing of the piezoelectric plate. Furthermore, in certain aspects of the present invention, it is an object to provide protection to the sensor electrical structures from the measured fluid, which may potentially be corrosive or hazardous, even when the fluid is under high pressure. It is a further object to protect the electrical structure without employing the sensor element as a diaphragm between the sensing environment and a low pressure cavity.

To that end there is provided a substrate for a piezoelectric sensor consisting of a composite of two nearly identical substrates. The composite substrate provides a self-passivating probe in which the active electrical connections and electrodes of the piezoelectric sensor are located at or near the centerline of the composite substrate and the outer surfaces are either grounded or electrically inactive.

The skilled in the art will recognize that the term electrodes may relate to ground electrodes, transducers (especially in the case of actively driving or driven electrodes) or other structures that cause or reflect perturbation in the piezoelectric crystal.

Therefore, in one aspect of the invention, there is provided a composite acoustic wave device (AWD) comprising a first and a second piezoelectric plates, each having an inner and an outer surface, wherein the inner surfaces of said plates are in face to face orientation. At least a first electrode is disposed between the respective inner surfaces of the first and second piezoelectric plates, and at least one return electrode. In certain embodiments, the return electrode is disposed on at least one of said outer surfaces. In more preferred embodiments, an additional, second electrode is further disposed between the first and second plates, in addition to the return electrode, however in some embodiments the second electrode is the return electrode.

Preferably, the first electrode and the second electrode each forms a respective parallel plate resonator with the return electrode, wherein the first and second electrodes are placed at sufficient proximity to allow transfer of acoustic energy between the first and second resonator. The first electrode or the second electrode, and optionally any number of other electrodes, may be single plate electrodes, or interdigitated electrode.

In one preferred embodiment of the present invention, the substrate is selected and the electrodes are constructed to impart displacement in said piezoelectric plates responsive to application of electrical charge between the electrodes where the displacement is substantially parallel to said outer surfaces. Such substrate selection, electrode construction and the resulting sensor is similar to the well-known thickness shear mode sensor.

Optionally, the AWD further comprises at least one coating disposed on at least a portion of at least one of said outer surfaces. It will be noted that a plurality of coating layers may exist and the term 'coating' as used herein refer to such plurality of coatings as a singular coating. The coating may be an abrasion resistant material, a chemically resistant material, a diamond-like carbon, a measurand sensitive coating such as a coating sensitive to presence or concentration of specific chemicals in the measured environment, or any desired combination of coatings.

In the preferred embodiment the first and second piezoelectric plates are of substantially similar dimensions. More preferably, the first and second piezoelectric plates have similar crystalline orientation.

While in the most preferred embodiment of the invention the first and/or second transducers (electrodes) are formed as single plate electrodes, interdigitated transducers are also contemplated.

In some embodiments, in order to obtain desired frequencies at least one of said plates, and preferably both, are provided with a depression in said outer surface.

In certain preferred embodiments of the invention, any AWD as described above may be provided with a depression in at least one of said inner surfaces. The depression defines a cavity between said first and second plates, so as to form an area of the sensor that is sensitive to pressure.

In yet another aspect of the invention, there is provided a sensor comprising a composite AWD similar to any AWD's described above. Further, circuitry couples electrical energy at least between the first electrode and the return electrode. Clearly it is desired to further have measurement circuitry to measure at least one parameter of said electrical energy, however such circuitry may be implemented separately.

The most preferred embodiment of this aspect of the invention, comprises a mounting bolt. Preferably, the circuitry or a portion thereof is embedded within the bolt, for example in the base of the bolt, while the AWD sensor element extends from the base into the measured substance. In embodiments having separate input and output transducers, the first electrode acts as an input transducer for introducing electrical signals into the AWD, and the second electrode acts as an output transducer for extracting electrical signals from the AWD. Typically the circuitry will comprise a signal source coupled to the input transducer for coupling input signal thereto, and measurement circuitry for measuring at least one relationship of the input and extracted signals.

Measured parameters may comprise one or more of any properties of the AWD that may be monitored electrically, such as, by way of example, the relative phase of the input and output signals, the individual or relative amplitudes of input and output signals, the frequency of a signal which maintains a constant phase shift, the delay time of a pulsed signal through the sensor, the impedance of a transducer, or any desired combination thereof.

In yet another embodiment of the invention there is provided a method of measuring at least one physical parameter of a substance without interference from high pressure, the method comprises the steps of placing any AWD as described above, or a portion of such AWD, in contact with said substance, coupling an electrical signal to the first electrode, and measuring the electrical signal extracted from the AWD. Where the extracted signal differs from said coupled signal and where the difference represents a measured parameter of the sensor. The parameter is known to be influenced by a physical or chemical measurand. Preferably, the step of measuring comprises measuring a parameter of the relationship between the extracted signal and the coupled signal, and the parameter is selected from a group consisting of frequency, insertion loss, phase, delay time, or any combination thereof. In the most preferred embodiments, the physical parameter to be measured is selected from a group comprising viscosity, density, temperature, pressure, chemical concentration, or a combination thereof.

In the most preferred embodiment, an AWD active electrodes form a first operative sensor as described. Further the AWD comprises a pressure sensor comprising a depression in at least one of said inner surfaces, and most preferably an identical depression in both inner surfaces. The depression defines a cavity between the first and second inner surfaces. A sensing element sensitive to pressure effects on the region of said plate having said depression, is disposed within the cavity. The sensing element may be a strain gage, or more preferably at least one transducer.

The most preferred embodiment calls for a depression of similar dimensions and oriented opposite in both inner surfaces such that the combination of the first and second depressions define the cavity, and further comprising a first input transducer and a first output transducer deposited on the first depression, and a second input transducer and a second output transducer deposited on the second depression.

The method or methods described above preferably further comprise the step of comparing the output of said first operative sensor with output obtained from said pressure sensor.

SHORT DESCRIPTION OF DRAWINGS

The summary above, and the following detailed description will be better understood in view of the enclosed drawings, which depict details of preferred embodiments. It should however be noted that the invention is not limited to the precise arrangement shown in the drawings and that the drawings are provided merely as examples.

DETAILED DESCRIPTION

The term composite substrate denotes at least two regions of substantially similar excitable substrate, which is commonly piezoelectric material but may also be magnetostrictive, electrostrictive, piezomagnetic, ferroelectric or ferromagnetic material, all of which will be generally described as excitable substrate and equivalently, related to as piezoelectric for clarity. The skilled in the art will recognize that the references to piezoelectric effect and piezoelectric substrate or material are universally applicable and intended to be inclusive of other methods by which an electric signal can cause acoustic or ultrasonic waves in the substrate and vice versa. In these specifications and the accompanied claims the regions will be commonly referred to as 'piezoelectric plates'. It should be clear that the term relates various shapes and cross-sections of any excitable substrate as desired to impart desired characteristics to the sensor. Furthermore it is noted that the structures and solutions described herein may be applicable to measuring at least one primary characteristic, and optionally a plurality of characteristics of the fluid, which will be related to as secondary characteristics, without any specific importance of one parameter over another. Thus, by way of a non limiting example, a primary characteristic may be viscosity, and the secondary characteristic may be density, as disclosed for example in my PCT patent application PCT/US2004/012546 or shear rate as disclosed in U.S. patent application Ser. No. 10/958,896.

In its most basic aspect, the present invention comprises a composite substrate of two piezoelectric plates of any excitable material as describe above. The two piezoelectric plates are preferably of similar dimensions and are of similar material, crystalline orientation and the like. The interface region of the two piezoelectric plates has at least one, and preferably a plurality of active electrodes. Several electrode arrangements are described below by way of non-limiting examples. A bonding agent is used for coupling the two piezoelectric plates together and to act as a seal isolating the electrodes from ambient environment. As no cavity is required between the piezoelectric plates, and as both plates are exposed to similar pressure, the plate bending stresses associated with asymmetric pressure are effectively neutralized. Therefore, while the piezoelectric material may compress, it will not bend or break until such pressure that will collapse the material. An additional advantage stems from the fact that the sensor has twice the effective transducer area, providing lower transducer impedance, and higher mass of piezoelectric material, and providing lower equivalent shear rate at a given acoustic power level. Utilizing the presently known art these improvements would require a doubling of the electrode area and a corresponding increase in the size and weight of the overall sensor package. Each of the above factors allows construction of higher quality sensor with minimal volumetric changes.

Figure 1:
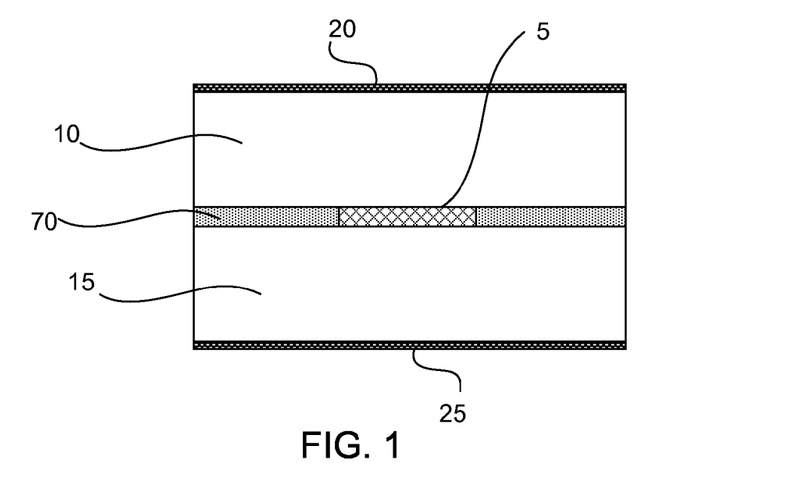
FIG. 1 depicts a cross section view of a basic embodiment of the invention.

In its most basic embodiment the invention comprises two similarly dimensioned piezoelectric plates (i.e. regions) 10,15 of excitable substrate each having at least one surface which is substantially flat and polished. The flat surfaces are termed 'inner surfaces' and face each other. Disposed between the flat surfaces is an active electrode 5. The two piezoelectric plates are bonded together with a bonding material 70 having compatible physical characteristics and good acoustic characteristics. Preferably the bonding material is a low melting temperature borosilicate glass, but the skilled in the art will recognize other suitable materials such as certain epoxy, thermoplastic and polyimide materials at low frequencies, silanes and siloxane wafer bonding methods at higher frequencies, and the like. Grounding electrodes, 20 and 25, are disposed on the outer surfaces of the plates. It is noted that an interdigitated transducer may be used instead of the single electrode 5, in which case the grounding electrodes are optional, and while the invention and claims extend to such embodiment, this embodiment is not shown as it will be clear to the skilled artisan.

Figure 2:
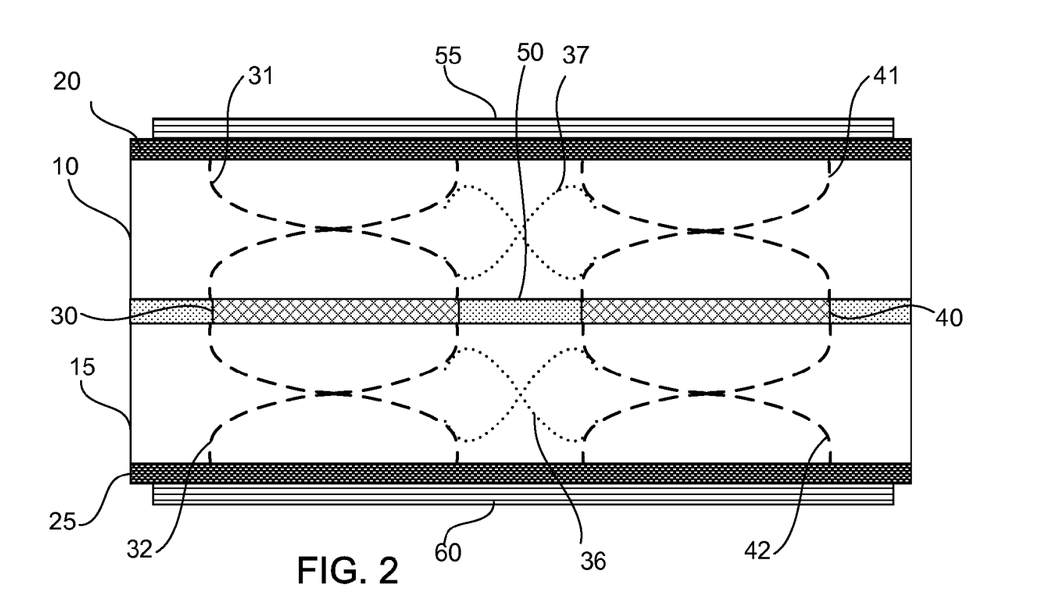
FIG. 2. depicts a simplified elevation cross section view of the most preferred embodiment of the invention.
Figure 3A:
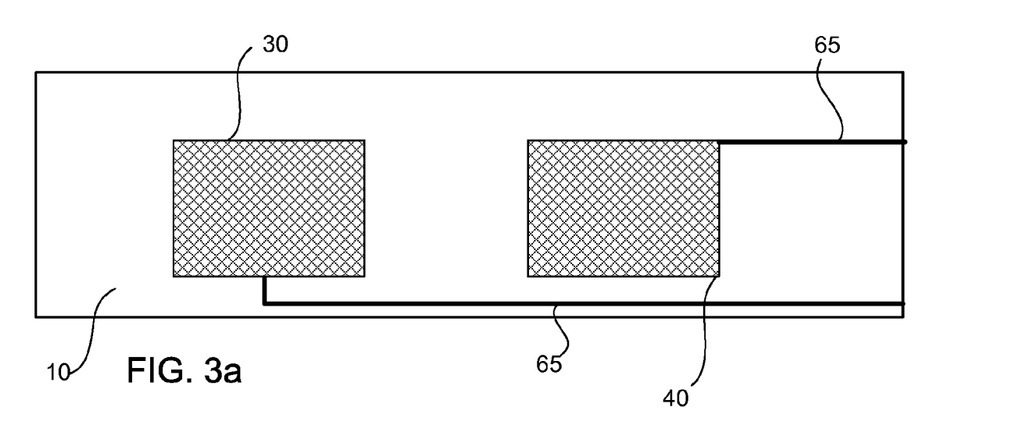
FIG. 3*a* depicts a preferred embodiment of the electrodes and electrical connections.
Figure 3B:
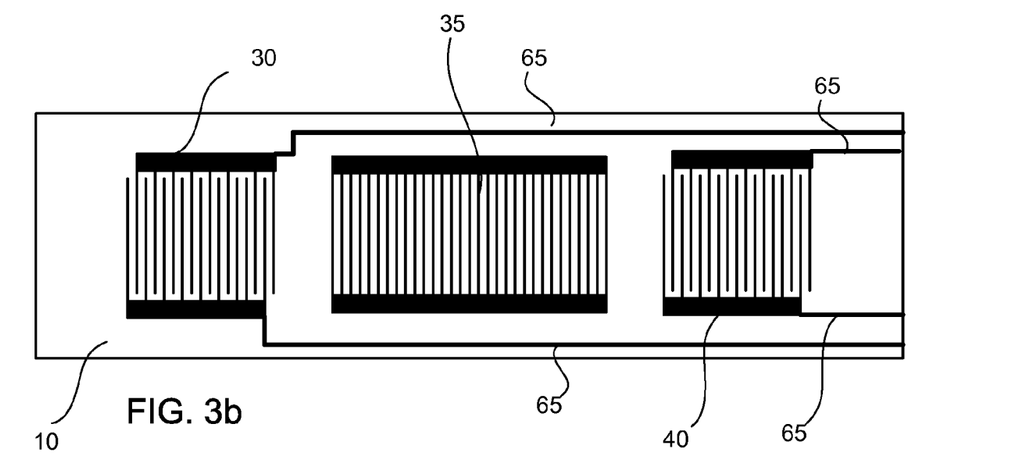
FIG. 3*b* depicts another preferred embodiment of the electrodes and electrical connections

FIG. 2 represents a more preferred embodiment of the invention. Similar to the simpler embodiments depicted in FIG. 1, the two piezoelectric plates 10 and 15 form the composite substrate. An input transducer 30 and an output transducer 40 are disposed between the two piezoelectric plates. The most preferred embodiment utilizes a single electrode for each transducer as seen in FIG. 3*a*. FIG. 3*b* shows an alternative embodiment that utilizes interdigitated transducers. If desired, in addition to the active electrodes of transducers 30 and 40, the region 50 intermediate to the two transducers may contain intermediate grating such as non-active electrode as is known to those skilled in the art. Preferably, optional ground electrodes 20 and 25 are disposed on the outer surfaces of the piezoelectric plates.

As can be seen by the schematic wave depictions 31 and 32 the input transducer 30 couples energy to both the upper 10 and lower 15 piezoelectric plates in a symmetrical, acoustical mirror-like fashion, which propagates to the coupled output transducer 40 as shown by the schematic wave depiction 41 and 42. Preferably the input and output transducers are placed in sufficient proximity to affect acoustic coupling 36, 37 between the transducers. Most preferably the distance between the transducers is selected so as to create a multi-pole resonator. The structure shown in FIG. 3*a* fits the so-called Monolithic Piezoelectric Sensor as disclosed in U.S. Pat. No. 6,033,852 to the present inventor. The structure shown in 3.*b*, fits AWD based on interdigital transducers (IDT) such as acoustic plate mode, Love wave, Lamb wave, SAW and the like.

Figure 4:
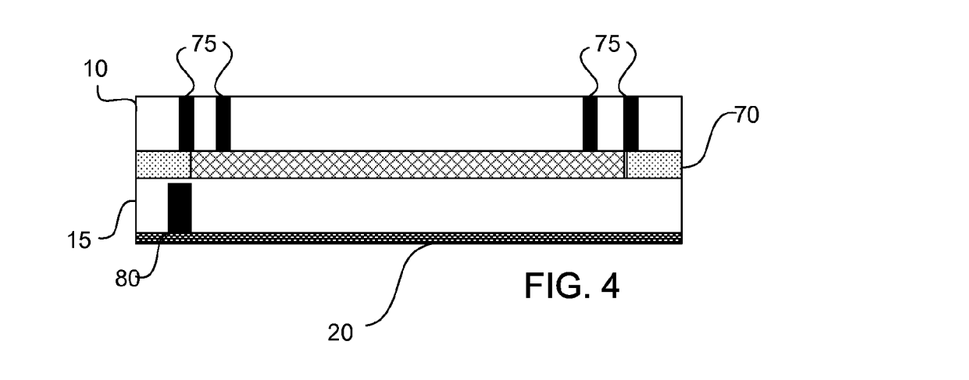
FIG. 4 depicts an edge view of the preferred embodiment showing electrical connections.

In the most preferred embodiment shown in FIG. 3*a*, simple plate electrodes are used for the input and output transducers 30 and 40 respectively. Both electrodes are deposited on the piezoelectric plate 10. In the embodiment shown in FIG. 3*b* the transducers 30 and 40 comprise periodic electrodes deposited on the inner surface of at least one the piezoelectric plates. FIG. 3*b* also depicts the optional intermediate grating 35. In both FIGS. 3*a* and 3*b* feed wires 65 extend from the transducers to the edge of the piezoelectric plate, where they wrap over the piezoelectric plate edge to form contact pads 75 as depicted in FIG. 4. FIG. 4 is a side view of the edge of the sensor, showing the two piezoelectric plates 10 and 15. The contacts 75 are electrically connected to the transducers and form convenient surface for providing connections to the sensor. Only one of the optional ground electrodes is shown 20, together with the corresponding ground contact pad 80.

The most preferred embodiment of the sensor element employs a single metal electrode for each of transducers 30 and 40 with the transducers referenced to the enclosing ground plane and forming parallel plate resonators. Each transducer establishes a parallel plate thickness mode resonance whose frequency is determined by the total thickness of the piezoelectric plate being a desired multiple of an acoustic wavelength with the relative thickness of the piezoelectric plates and therefore the position of the active metal region, more or less corresponding to a peak of the electrical potential associated with the desired multiple. Most preferably, it is desirable that the multiple be one and that the respective piezoelectric plates will be of essentially identical thicknesses. Proper selection of the spacing between transducers 30 and 40 allows energy inserted into transducer 30 to couple to the resonator formed by transducer 40 and vice versa, as shown by dotted lines 36 and 37. The resulting coupled resonator filter offers numerous advantages over other sensors, especially when constructed in accordance with the present invention. These advantages include simple metal patterning, extremely low acoustic power levels in the bonding material region, and excellent control of sensor shear rate. Since to-date applicability of these structures to liquid phase sensing has been limited by both pressure effects and excessive transducer impedance, the present invention is especially beneficial as it compensates pressure effects and halves the transducer impedance.

Figure 5:
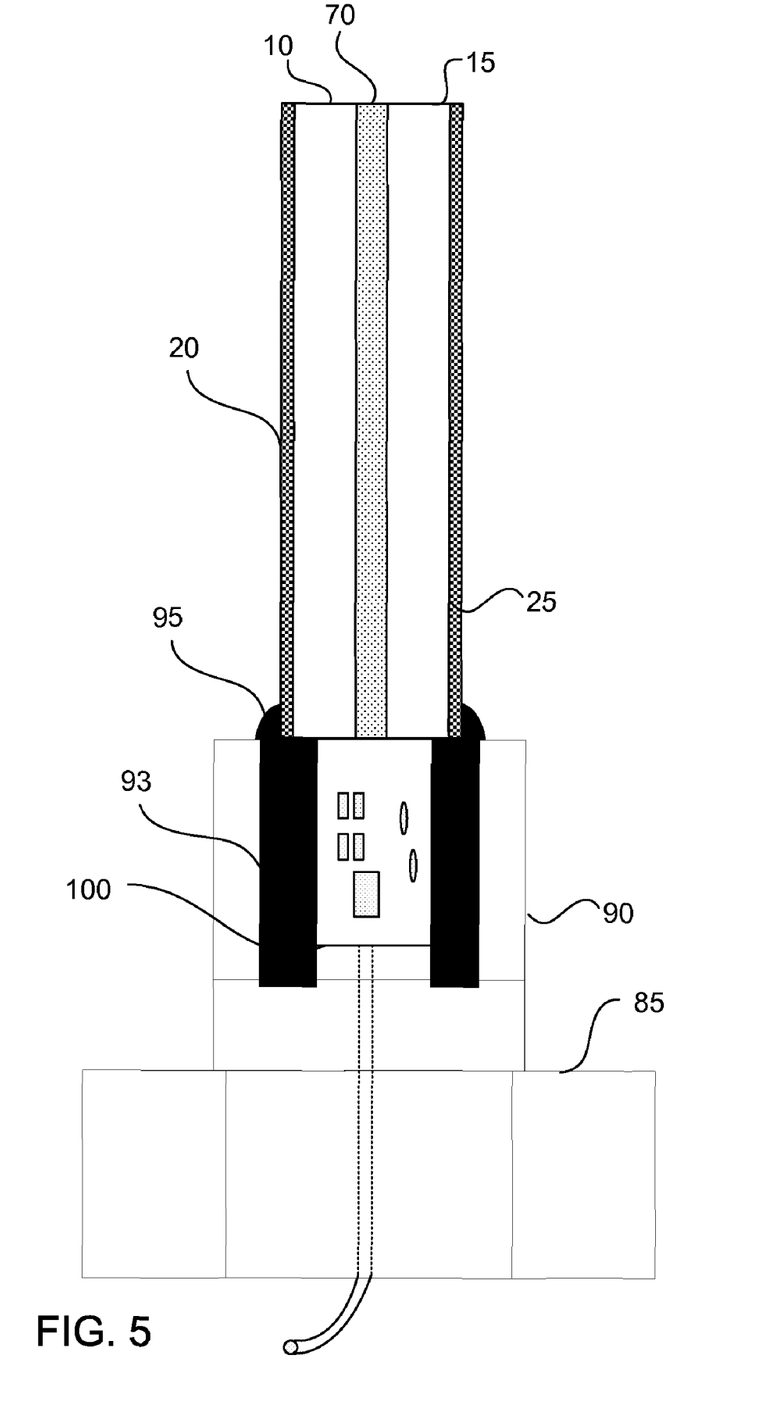
FIG. 5 depicts a sensor attached to a bolt which represents the most preferred mounting method.

The most preferred embodiment calls for mounting the sensor element to a carrier such as a bolt 85, so as to form a sensor assembly for easy deployment. FIG. 5 depicts a simplified embodiment of such assembly. The sensor is coupled on its edge to the bolt at or near the bolt's threaded portion 90. Electrical contacts are provided to match the contact pads 75 and 80. High pressure sealing agent 95 is applied to both support the sensor element on the bolt, and to isolate the contacts from the environment. The sealing agent may be of any material and of any thickness required to withstand the pressure and the ambient environment. In one preferred embodiment ceramic material is used as the sealant. Borosilicate glass, epoxy, silicone and polyimide, and equivalents are further examples that will be recognized by the skilled person as suitable sealants.

While the electrical contacts of the bolt mounted sensor may be fed to supporting electronics separate from the sensor, in the most preferred embodiment the support electronic circuitry 100 is embedded in the sensor assembly, and only conditioned and normalized data is sent from the assembly. In a preferred embodiment the circuitry is placed within the bolt. By way of non-limiting example, the circuitry may comprise radio frequency circuitry to excite and measure the acoustic waves, frequency counting, power detection and/or phase measurement circuitry to convert the radio frequency signals into a sensor response, an analog to digital interface and a microprocessor having a suitable digital interface to the external control system or any combination of these and other desired circuitry.

In the most preferred embodiment, the sensor element is mounted to a mount 93 which comprises a Low Temperature Co-fired Ceramic (LTCC) or similar hybrid circuit 93 that incorporates the electronic circuitry and is bonded to the sensor edge having the contact pads. The mount is coupled to the bolt by any desired method such as threading, bonding and the like. In such embodiment, the high pressure seal 95 is preferably formed as a part of the mount 93.

It is desirable but not mandatory, that the bonding agent between the two piezoelectric plates will be significantly thinner than the effective piezoelectric plate thickness. The ideal bonding material will have high quality acoustic characteristics, adhere tightly to all features so as to prevent voids, and will be thermally compatible with the plate material or sufficiently plastic to allow for thermal expansion. As it is located between the piezoelectric plates it will also have minimal effect on the energy transfer between the transducers and the plates. The skilled in the art will recognize however that the piezoelectric plates may be located at any desired distance from each other, as long as the space between the two plates is filled with the bonding agent or other material which counteracts the pressure effects and the transducers are located at equivalent maxima of the standing wave. Thus, if desired an intermediate layer may be disposed between the piezoelectric plates. Clearly, in such an embodiment separate transducers will be required for each of piezoelectric plates.

Figure 6:
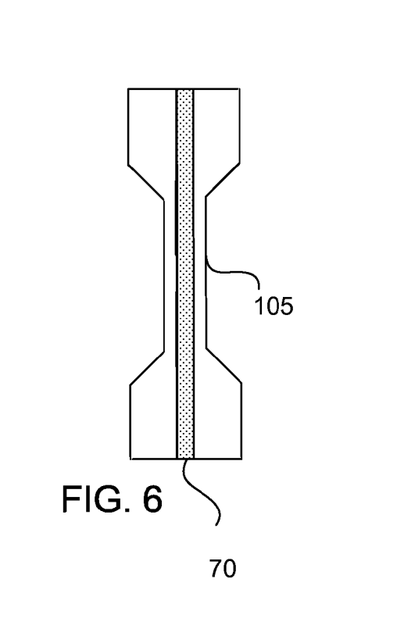
FIG. 6 depicts an etched membrane embodiment.

The preferred method of making the device involves slicing a crystal into parallel wafers. Polishing at least one surface of each wafer, and more preferably both surfaces. If one or more non-flat surfaces are desired, the desired shape is etched or otherwise formed into the surface. Non-limiting examples include textured surfaces to form liquid traps for density measurement, cylindrical, elliptical or circular contouring for enhanced energy trapping of the acoustic wave, and etched thin membranes. In one preferred embodiment depicted in FIG. 6 an etched membrane construction is depicted where a depression 105 is formed in the outer piezoelectric plate face so as to achieve a desired high operating frequency and mass sensitivity while maintaining a thicker, more robust support region.

Once the piezoelectric plate surfaces are of the desired form and smoothness, the side that will become the outer sensor surface of all piezoelectric plates is optionally metalized. Active electrodes are deposited on the opposite surface of at least half the plates. Electrical connections are also brought to the piezoelectric plate edge. Each pair of piezoelectric plates are bonded together and the sensor element is mounted to a mount 93. Clearly other methods will be available. One such method involves depositing electrodes on the inner sides of the each piezoelectric plate and bonding which either allows contact between the two electrode sets or not, as desired.

Figure 7:
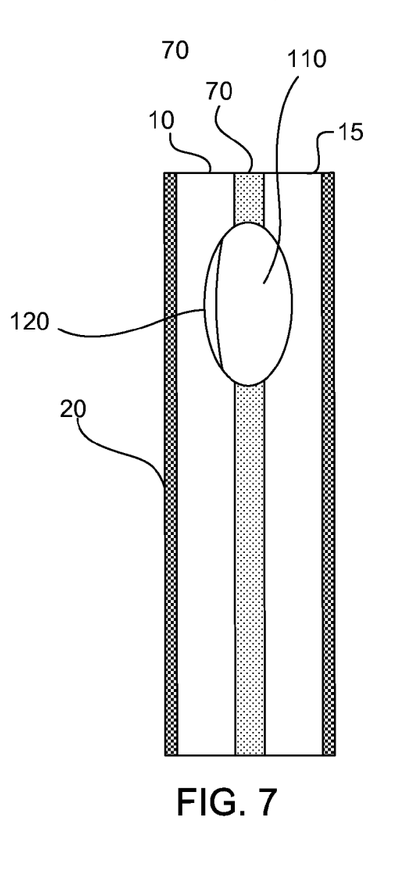
FIG. 7 depicts an embodiment of a combined pressure and viscosity sensor.

A primary advantage of the present invention is avoiding the plate bending strain stemming from the pressure differential between the outer and inner piezoelectric plate surfaces in solutions provided by the prior art. However it is also important to realize that this pressure differential may be used beneficially under certain circumstances. Thus for example, as depicted in FIG. 7, a cavity 110 of carefully selected dimensions may be provided at a separate section of the sensor, between the two piezoelectric plates. A stress sensor, such as MEMS, strain gage, or preferably interdigitated transducer 120 is deposited within the cavity and is used to measure the bending strain that is directly related to the pressure of the medium being measured. The sensor thus provides combined measurements of pressure in addition to the primary measured parameter.

Figure 8:
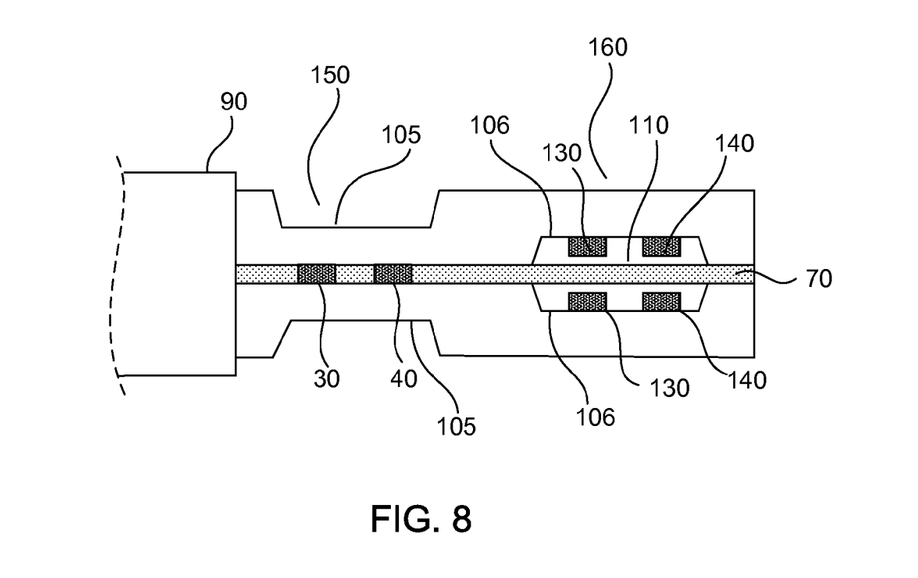
FIG. 8 depicts a preferred embodiment of a combined sensor, in which complementary pressure-sensitive and pressure-insensitive structures are implemented.

FIG. 8 depicts a preferred embodiment of a combined measurand sensor where one of the measurands is pressure. It comprises essentially two complementary sensors located in different portions of the piezoelectric plates. A first sensor 150, is formed substantially as described in any of the examples above, and for measuring any desired measurand or measurands. Sensor 150 is provided with depressions 105 on the outer side of the piezoelectric plates, as described above. A complementary second sensor 160 is formed with similar depressions 106 etched into the opposite (inner) piezoelectric plate surfaces, so as to form a cavity 110 when the piezoelectric plates inner surfaces face each other. The two sensors have similar total thickness and impedance in their respective active regions. The two sensors may employ any desired transducer style. The preferred embodiment utilizes the single electrode transducer for each of the input transducers 30 and 130, and output transducers 40 and 140. Preferably each piezoelectric plate 10 and 15 has similar transducer arrangement, so if two transducers are used for the first sensor 150, two transducers 130 and 140 are employed on each of the piezoelectric plates respectively in the second transducer 160. Because the first and second sensors 150 and 160 have similar impedance, mass, frequency and sensitivity, they are well matched in the absence of pressure. Since the first sensor is designed to have very low sensitivity to pressure and the second sensor is designed using an internal cavity 110, known to incur pressure sensitivity, the combination of the first and second sensors form a differential pair, allowing precise measurement of the pressure effects, while utilizing only one piezoelectric structure. Furthermore, the measured pressure may be used to provide a correction for any residual pressure effects in the pressure insensitive first sensor, allowing even more precise measurement of the measurand/s of the first sensor portion.

Further optionally, one or more coating layers, collectively referred to as the coating, may be applied to the outer surfaces of the sensor or portions thereof. Such coating 55 and 60 may provide desired characteristics such as preventing adhesion of the measured substance, resisting abrasion, providing chemical resistance and the like. In a preferred embodiment such coating is achieved by depositing diamond-like carbon, boron nitride, silicon-aluminum oxynitride or similar materials on the probe. In the most preferred embodiment a fluorinated diamond like carbon layer is deposited over a refractory metal ground plane.

Optionally, the probe may be adapted for detecting of specific substances by depositing a substance sensitive film, preferably as the outermost layer of the coating 55, 60 on the substrate, whether directly or indirectly. The substance sensitive film may be a polymer, biochemical, metal oxide or metallic film or other material that is chemically structured to capture specific molecules or molecule groups. When such molecules are trapped, the change in the physical properties of the film (e.g. mass, stiffness, viscosity or conductivity) cause a change in the signal propagating characteristics, which can be measured to detect the presence of such molecules. Such structure makes the sensor easily applicable to detection of even small amounts of biochemical substances by using enzyme, antibody, antigen, or nucleic acid molecules as the coating. The use of electrochemical methods on a metallic film is also contemplated for trace dissolved metals. Such a sensor comprises an outer conductor which may be connected to any potential, and employed as the working electrode of an electrochemical cell. The skilled in the art will be aware of numerous other chemically selective coatings that might be applied and chemically selective sensors that might result from such combinations.

The selection of piezoelectric materials, orientations, device geometries, and corresponding transducers to achieve various physical parameters such as energy levels, best fit for the desired measurand, achieving optimal sensor characteristics, and the like, is within the capacity of the skilled in the art in light of the teaching of the different aspects of the present invention, and are a matter of technical choice. Similarly, the selection of the proper support circuitry and instrumentation is a matter of technical choice to best fit the desired end results, and will vary greatly according to different embodiment, but be clear to the skilled artisan.

Figure 9:
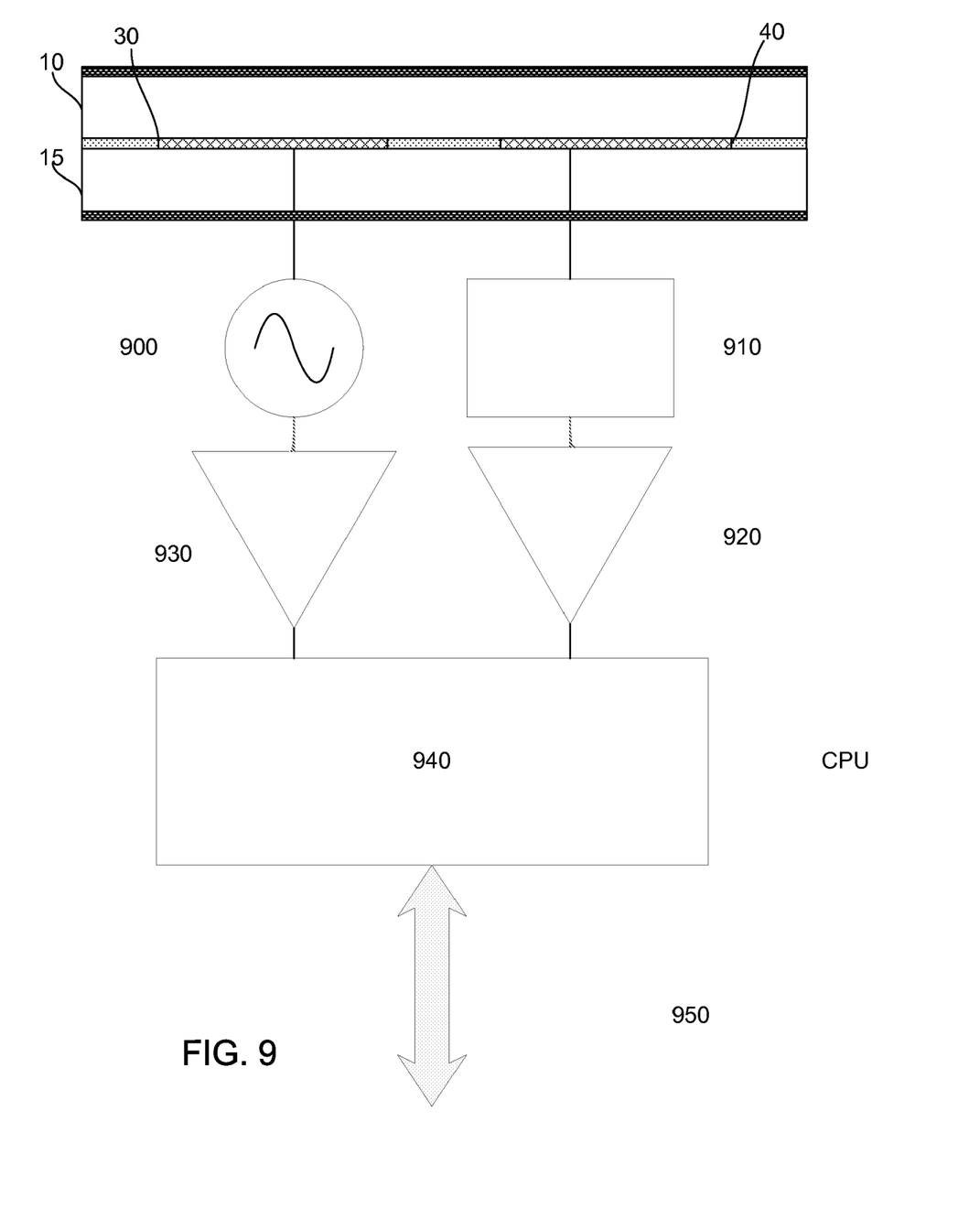
FIG. 9 depicts a simplified diagram o preferred electronic circuitry coupled to the sensor element.

FIG. 9 depicts a simplified diagram of the preferred electronic circuitry coupled to the sensor element. In the preferred embodiment a two transducer structure is employed, offering a distinct input and output signal. A signal source 900 is applied to the input transducer 30 and a signal detector 910 monitors the output transducer 40. Data converters 920 and 930 convert the signals of the output and input transducers respectively, for a signal that can be interpreted by CPU 940. The signals are compared by the CPU and the relationship is interpreted as the sensor's measurand. The CPU transmits the measurement results via digital bus 950.

Figure 10:
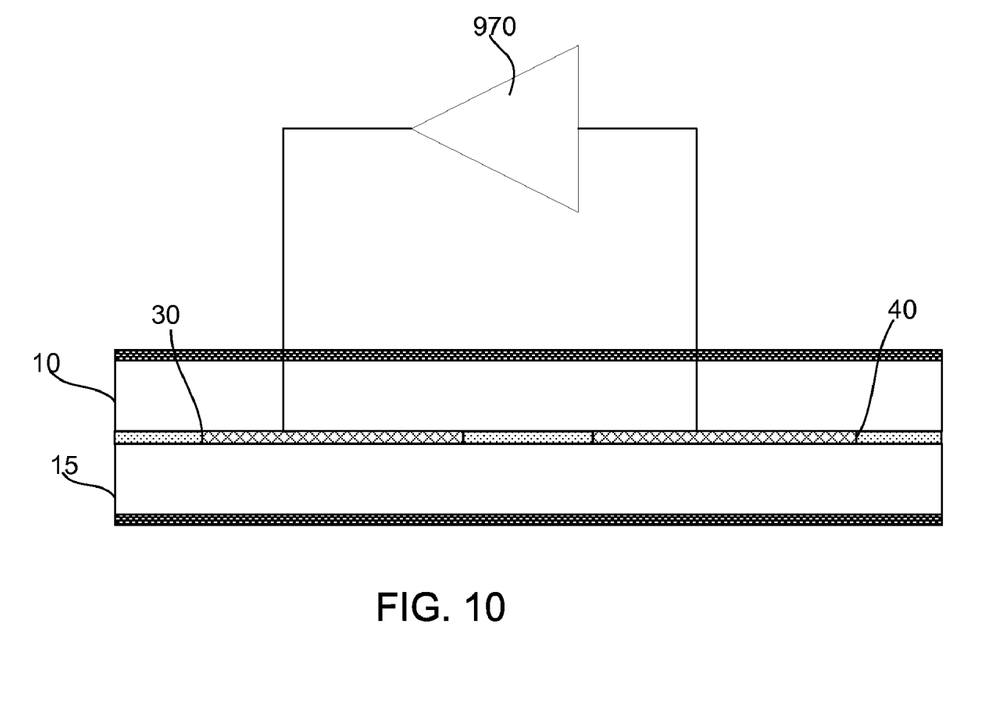
FIG. 10 is a simple drive circuitry for a sensor acting as a part on an oscillator.

In the case of an AWD with a single transducer, the output signal is the reflected portion of the input signal. These may be directly compared using an impedance analyzer, separated using a directional coupler, or indirectly monitored using the AWD to control an impedance-based oscillator of Collpitts, Pierce, or similar configuration. Those measurements methods will be clear to the skilled in the art. The most preferred embodiment of the sensor assembly circuitry employs the sensor element as a series feedback element in a loop oscillator, as seen in FIG. 10. The oscillator comprises the sensor as a natural crystal, and an amplifier 970 coupled between the input and output transducers. The oscillator serves to measure the output signal, apply an input signal as an amplified replica of the output signal, and to continuously evaluate a preselected phase and amplitude relationship between the signals. Such an oscillator spontaneously creates a signal at the frequency for which the feedback loop has a multiple of 360° phase shift. The amplitude of the signal is determined such that the insertion loss of the sensor and the saturated gain of the amplifier are in balance. The measurand is determined by monitoring the insertion loss of the sensor and/or frequency of the signal at the spontaneous oscillation point.

It will be appreciated that the invention is not limited to what has been described herein above merely by way of example. While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

What is claimed is:

1. A composite acoustic wave device (AWD) comprising:
   a first and a second piezoelectric plates, each having an inner and an outer surface, wherein said inner surfaces of said plates are joined in face to face orientation;
   at least a first electrode disposed between the respective inner surfaces of said first and second piezoelectric plates, and
   at least one return electrode;
   wherein said composite acoustic wave device forms a thickness shear mode resonator;
   wherein the separation between said outer surfaces being approximately an integral number of wavelengths near a resonant frequency of said AWD; and,
   wherein said first electrode being located substantially at a peak of the electrical potential of said resonant frequency.

2. A composite AWD as claimed in claim 1 wherein said return electrode is disposed on at least one of said outer surfaces.

3. A composite AWD as claimed in claim 1, further comprising a second electrode disposed between said first and second plates.

4. A composite AWD as claimed in claim 3, wherein said return electrode is disposed on at least one of said outer surfaces, and wherein said first electrode and said second electrode each forming a respective parallel plate transducer with said return electrode, and wherein said first and second electrodes are placed at sufficient proximity to allow transfer of acoustic energy between said first and second parallel plate transducers.

5. A composite AWD as in claim 4 further comprising a second return electrode oppositely disposed on said second outer surface.

6. A composite AWD as claimed in claim 1 further comprising a coating disposed on at least a portion of at least one of said outer surfaces.

7. A composite AWD as claimed in claim 6 wherein said coating comprises an abrasion resistant material.

8. A composite AWD as claimed in claim 6 wherein said coating comprises chemically resistant material.

9. A composite AWD as claimed in claim 6 wherein said coating comprises diamond-like carbon.

10. A composite AWD as claimed in claim 6 wherein said coating is measurand sensitive.

11. A composite AWD as claimed in claim 1, wherein said first and second piezoelectric plates are of substantially similar dimensions.

12. A composite AWD as claimed in claim 1, wherein said first and second piezoelectric plates have similar crystalline orientation.

13. A composite AWD as claimed in claim 1, wherein at least one of said plates is provided with a depression in said outer surface.

14. A sensor comprising:
a composite AWD comprising:
   a first and a second piezoelectric plates, each having an inner and an outer surface, wherein said inner surfaces of said plates are joined in face to face orientation;
   at least a first electrode disposed between the respective inner surfaces of said first and second piezoelectric plates, and
   at least one return electrode;
   wherein said composite acoustic wave device forms a thickness shear mode resonator having a separation between said outer surfaces being approximately an integral number of wavelengths near a resonant frequency of said AWD; and,
   wherein said first electrode being located substantially at a peak of the electrical potential of said resonant frequency;
said sensor further comprising circuitry to couple electrical energy at least between said first electrode and said return electrode.

15. A sensor as claimed in claim 14, further comprising measurement circuitry to measure at least one parameter of said electrical energy.

16. A sensor as claimed in claim 14 further comprising a mounting bolt coupled to said composite AWD.

17. A sensor as claimed in claim 16 wherein said circuitry or a portion thereof is embedded within said bolt.

18. A sensor comprising:
a composite AWD comprising:
   a first and a second piezoelectric plates, each having an inner and an outer surface, wherein said inner surfaces of said plates are joined in face to face orientation;
   at least a first electrode disposed between the respective inner surfaces of said first and second piezoelectric plates, and
   a first and a second return electrodes, each disposed on an opposing outer surface;
   wherein said composite acoustic wave device forms a thickness shear mode resonator having a separation between said outer surfaces being approximately an integral number of wavelengths near a resonant frequency of said AWD; and,
   wherein said first electrode being located substantially at a peak of the electrical potential of said resonant frequency;
said sensor further comprising circuitry to couple electrical energy at least between said first electrode and said first and second return electrodes.

19. A sensor as claimed in claim 18, further comprising measurement circuitry to measure at least one parameter of said electrical energy.

20. A sensor as claimed in claim 18 further comprising a mounting bolt coupled to said AWD.

21. A sensor as claimed in claim 20 wherein said circuitry or a portion thereof is embedded within said bolt.

22. A sensor as claimed in claim 18, further comprising a second electrode disposed between the respective inner surfaces of said first and second piezoelectric plates;
   measurement circuitry to couple electrical energy at least between said second electrode and said first and second return electrodes to measure at least one parameter of said electrical energy.

23. A sensor as claimed in claim 22 further comprising a mounting bolt coupled to said AWD.

24. A sensor as claimed in claim 23 wherein said circuitry or a portion thereof is embedded within said bolt.

25. A composite acoustic wave device (AWD) comprising:
   a first and a second piezoelectric plates having substantially similar dimensions and similar crystalline orientation, each having an inner and an outer surface, wherein the separation between said outer surfaces determines a resonant frequency of said AWD, and wherein said inner surfaces of said plates are joined in face to face orientation;
   at least a first electrode disposed between the respective inner surfaces of said first and second piezoelectric plates, and
   a return electrode disposed between the respective inner surfaces of said first and second piezoelectric plates;
   wherein said composite acoustic wave device forms a thickness shear mode resonator.

* * * * *